United States Patent [19]

Ali et al.

[11] 4,454,226

[45] * Jun. 12, 1984

[54] ENZYMATIC IMMUNOASSAY

[76] Inventors: Majid Ali, 19 Edgemont Pl., Teaneck, N.J. 07666; Donald Nalebuff, 89 Lakeshore Dr., Oakland, N.J. 07436; Alfred Fayemi, 15 Francine Ct., White Plains, N.Y. 10607; Madhava P. Ramanarayanan, 271 Briarcliffe Rd., Teaneck, N.J. 07666; Ricardo Mesa-Tejada, 42 Juniper Pl., Briarcliff Manor, N.Y. 10510

[ * ] Notice: The portion of the term of this patent subsequent to Mar. 19, 1998 has been disclaimed.

[21] Appl. No.: 358,888

[22] Filed: Mar. 17, 1982

[51] Int. Cl.³ ..................... G01N 33/54; C12N 9/96; C12N 11/02; C12Q 1/28
[52] U.S. Cl. .................................. 435/7; 435/188; 435/177; 435/28; 436/513; 436/531
[58] Field of Search ............... 435/7, 28, 188, 177; 436/513, 531

[56] References Cited

U.S. PATENT DOCUMENTS

| 3,654,090 | 4/1972 | Schuurs et al. | 435/188 |
| 4,002,532 | 1/1977 | Weltman et al. | 435/7 |
| 4,169,012 | 9/1979 | Dawson et al. | 435/188 |
| 4,347,311 | 8/1982 | Schmitz | 435/188 |
| 4,356,833 | 3/1982 | Ali et al. | 435/188 |

OTHER PUBLICATIONS

Avrameas et al., "Coupling of Enzymes to Antibodies and Antigens".
Scand Journal of Immunology 8 (Supp. 7) (1978) pp. 7–23.
Mukojima et al., "Enzyme Immunoassay Using Multiple Antigen-Enzyme Complex".
Rinsho Kagaku Shimpojumu 16 (1976) pp. 42–46 Chem. Abst. 87: 180244k.
Zeiss et al., "Quantitation of IgE Antibody Specific for Ragweed and Grass Allergens: Binding of Radiolabeled Alergens by . . . ".
Journal of Allergy and Clinical Immunology 62(2) (1978) pp. 83–90.
Nakane et al., "Peroxidase Labeled Antibody, New Method of Conjugation".
Journal of Histochemistry and Cytochemistry 22 (12) (1974) pp. 1084–1091, Chem. Abst. 82: 41694r.
Lehninger, "Biochemistry" 2nd Edition, Worth Publishers, Inc. (1975). pp. 102–104.
Berezin et al., "Catalytic Properties and Thermostability of Horseradish Peroxidase Covalently Bound to Sepharose Through . . . ".
Biokhimiya 42 (5) (1977) pp. 926–933 Chem. Abst. 87: 35084d.
Schroeder et al, "Enzyme Immunoassays for Quantitative and Qualitative Analysis of Alergen Extracts".
Adv. Allergol. Clin. Immunol. Proc. Congr. Allergol. 10th 1979 pp. 513–519, Chem. Abst. 94: 172587d.
Sigma Chemical Company, "Biochemical and Organic Compounds" Feb. 1983, p. 605.

Primary Examiner—Robert J. Warden
Assistant Examiner—John Edward Tarcza
Attorney, Agent, or Firm—Ostrolenk, Faber, Gerb & Soffen

[57] ABSTRACT

An enzyme immunoassay for detecting an antigen in a biologic fluid or tissue which comprises contacting the fluid or tissue with an antibody specific for the antigen under binding conditions, at least one of the fluid or tissue and antibody having a solid component, contacting the resulting solid with a conjugate bindable with the antibody under binding conditions and determining the enzyme activity of the resulting solid phase is described. The conjugate is of peroxidase and an allergen, non-immunoglobulin protein or primary amino group containing drug having an average of 2-3 molecules of peroxidase per molecule of substance with an average molecular weight of about 30,000 daltons, prepared by reacting peroxidase previously treated with phenyl isothiocyanate and oxidized to form aldehyde groups with the substance to form a Schiff's base which is titrated with a reducing agent to form a stable conjugate.

11 Claims, 1 Drawing Figure

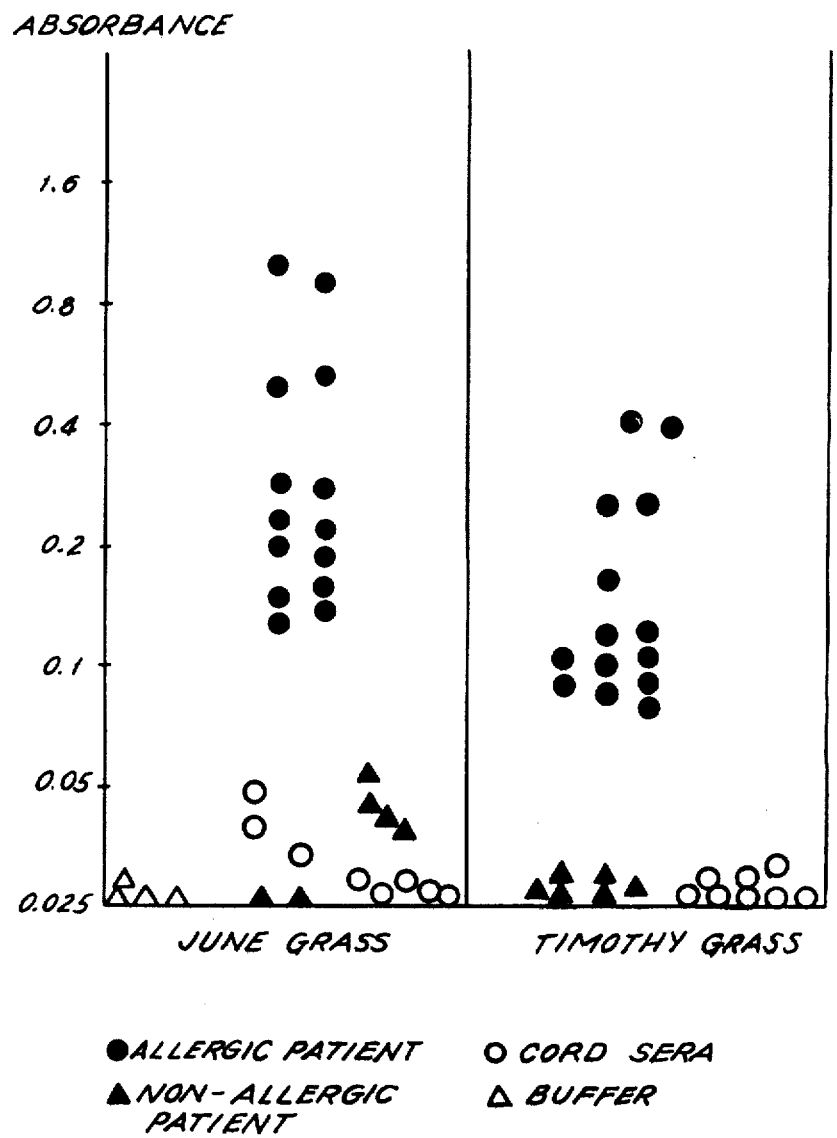

ENZYMATIC IMMUNOASSAY

BACKGROUND OF THE INVENTION

In 1966, Ishizaka established that the human allergen reaginic antibodies belong to a distinct class of immunoglobulins, IgE. There followed a decade of remarkable sequence of events. Sensitization of the human and monkey skin to Prausnitz-Küstner reaction by IgE antibodies was demonstrated. It was recognized that the role of IgE is central to the release mechanisms of chemical mediators of anaphylaxis; it mediates immunologic release of histamine from human leucocytes and mast cells; it primes the human lung tissue for antigen-induced release of histamine and Slow Reacting Substance of Anaphylaxis; it triggers the release of eosinophil chemotactic factor from human lung; and its affinity for attachment, through its Fc portion, to the receptors on the surface of mast cells and basophil granules was shown. It has been inferred that the number and the affinity of IgE antibodies bound to the basophil granulocytes determines the sensitivity of this cell to the allergen, while the histamine release induced by the antigen-antibody reaction on the cell surface is the function of the intracellular enzyme system and cyclic AMP level.

Dating back to the early part of the 20th century, patients with hay fever were treated with injections of incriminated allergens, albeit without understanding the pathologic bases of the disease or the pharmacologic bases for the efficacy of the therapy. Johansson's observation, in 1967, of augmented levels of serum IgE in atopic patients sparked intense interest in this relationship. Individuals with inhalant allergies were found to display seasonal peaks in their serum IgE levels; abatement of allergic symptomatology with immunotherapy was documented. Partial suppression of seasonal peaks following specific immunotherapy was demonstrated and the interrelationship of levels of IgE and IgG in atopic subjects, and the changes induced by specific immunotherapy have been illuminated.

The major in vitro test used to determine IgE today is a radioimmunoassay technique known as the Radio Allergo Sorbent Test or RAST. A major improvement in this technique is described in Nalebuff U.S. Pat. No. 4,243,641.

The advent of enzyme-labeled antibodies has been a major event in the progress of immunoassays. The use of such enzyme labels, for this purpose introduced in 1971, offers several advantages over radioimmunoassay techniques including the freedom from hazards of radioactive material, the stability of a label for months and possibly longer, the use of photometric rather than radiometric equipment, and at times, elimination of separation procedures. For these reasons, enzyme immunoassays have found widespread and diversified application both in reasearch and in clinical practice.

In 1966, Nakane & Pierce published a report demonstrating that peroxidase could be coupled to an antibody by a simple procedure to produce a stable conjugate. The intact immunological reactivity of such a conjugate was shown to render it eminently suitable for use in immunotracing methods, in a fashion similar to that of fluorescein-labeled antibody. Since that time a number of conjugates have been developed and used for enzymatic immunological tests. See, e.g., U.S. Pat. Nos. 4,016,043 and 3,645,852.

For the assay of total IgE in serum, alkaline phosphatase has been employed as the enzyme marker in an application of the enzyme linked immunosorbent assay and in a magnetic enzyme immunoassay. The use of both alkaline phosphatase and galactosidase has been described for the assay of allergen-specific IgE antibodies. The success in terms of quantitation, sensitivity and absence of non-specific reaction in any solid phase immunoenzymatic technique depends, to a great extent, on the quality of the enzyme-antibody conjugate. The immunoenzymatic techniques described in the literature for use with IgE have been performed using conjugate prepared by means of bifunctional reagents. Thus, the use of alkaline phosphatase (molecular weight 60,000) or galactosidase (molecular weight 580,000) as enzyme markers has required the use of glutaraldyde for conjugation of the enzyme to the antibody. The negative controls of such procedures exhibit a high degree of background activity or interference which interferes with the readability, i.e., interpretation, of the test results. While no precise quantitation has been reported, we have found that the use of alkaline phosphatase and galactosidase as enzyme markers has resulted in the final yield of a very small amount of functionally usable conjugates, usually 30% or less, and unacceptable contamination with large amounts of side reaction products. Such by-products include enzyme-enzyme conjugates, IgG-IgG conjugates and large aggregates. The separation of the usable conjugate from the undesirable side reaction products has been tedious and time consuming and, in addition, the stability of the purified fraction has not been satisfactory.

Recently, a hetero-bifunctional reagent, N-succinimidyl 3-(2-pyridyldithio) propionate (SPDP) has been successfully used for the conjugation process. In this procedure, SPDP reacts specifically with primary amino groups of proteins to produce a 2-pyridyl disulfide derivative. One of the proteins is thiolated by an additional reduction step under conditions which do not affect native disulfide bonds. The two modified proteins are then linked by a disulfide bond. Using B-galactosidase conjugates of anti-human IgE prepared by the above procedure, enzyme immunoassays for the determination of total IgE and allergen-specific IgE have been developed.

An in vitro solid phase immunoenzymatic allergy test for the presence of IgE which is very successful in terms of quantification, sensitivity and absence of non-specific reaction is described in our U.S. Pat. No. 4,256,833. In this test, the enzyme employed is horseradish peroxidase (HRPO, molecular weight 40,000) and the conjugate is prepared using the enzyme with its free amino groups blocked with phenylisothiocyanate as the first step and the reduction of the conjugate is carried out by titration.

An inherent weakness in the immunoassays for IgE are that these assays fail to prevent interference by antibodies which do not belong to the IgE class of immunoglobulins but have specificity for the particular allergen under study. Such antibodies are generally regarded as belonging to IgG and IgA classes of antibodies. For example, immuno therapy with pollen antigens and bee venom results in a gradual fall in the level of allergen specific IgE antibodies, a rise in allergen specific IgG and allergen specific IgA antibodies, and a decline in basophil responsiveness. Naturally occurring IgG and IgA antibodies with an affinity for various allergens also occur in patients with inhalant allergy.

The presence in serum of these "blocking" antibodies has been demonstrated by two approaches. First, the serum containing these antibodies can inhibit the antigen-induced release of histamine from basophils of sensitive patients, and second, such serum can inhibit the RAST test after IgE in serum has been inactivated with heat. The competition of IgG and IgA antibodies with the allergen specific IgE antibodies for allergen linked to an immunosorbent has been shown to occur with microcrystalline cellulose as well as with filter paper discs used in the commercially available RAST test. In the second step of the RAST assay, the binding of a labeled antibody to allergen-specific IgE antibodies is proportionally reduced and this may result in underestimation of the quantity of specific IgE in the test sample.

The IgG and IgA antibody interference not only impairs the diagnostic efficiency of the RAST test and the enzyme immunoassays for specific IgE, but it also masks the impact of immunotherapy on the serum levels of specific IgE and IgG antibodies. It is well established that specific immunotherapy results in the production of allergen-specific IgG antibodies and the conventional RAST and enzyme immunoassay techniques are therefore likely to produce spuriously low results for serum levels of IgE antibodies in this setting. This may also occur in allergic patients with high titers of naturally occurring IgG and IgA antibodies with specificity for the allergen under investigation.

Similar problems are also encountered in the use of the enzyme-labeled antibodies in histochemical localization of antigenic substances in the tissues. The use of antibody-antigen reactivity for determining the presence of various substances in animal tissue is known. For example, if one were seeking to determine whether insulin was present in a given tissue sample, the tissue would be contacted with antibody for insulin. The two Fab portions of the antibody combine with the insulin in the tissue and the Fc part is available for binding to a second antibody against the immunoglobulin G of the first species. A labeled second antibody is then reacted with the test system and an analysis is made for the label. Unfortunately, a preparation of anti-insulin antibody in the easily available form is a purified IgG fraction which in addition to specific antibodies to insulin also contains, in excess, other unwanted IgG molecules which include heterophile antibodies, naturally occurring antibodies and the like. Such unwanted IgG molecules can have the ability to bind indiscriminately to tissue components and thus render the specific localization of insulin highly ambiguous.

Unambiguous localization of a given antigen by the principle outlined above is possible only through the use of antibodies purified by affinity chromatography, which at present is prohibitively expensive.

In our U.S. Pat. No. 4,256,833, we describe a stable peroxidase immunoglobulin conjugate which is used in an enzyme immunoassay in which an allergen is immobilized on a solid phase, the test serum is incubated with the immobilized allergen and the amount of specific IgE bound to the allergen is quantified by incubating it with the enzyme labeled immunoglobulin.

It is the object of this invention to provide a new and improved method and reagent for carrying out an immunoenzymatic test for the presence of allergen-specific IgE, for proteins not belonging to the immunoglobulin class and for drugs which have or can be made to have a primary amino group.

This and other objects of the invention will become apparent to those skilled in this art from the following detailed description.

SUMMARY OF THE INVENTION

This invention relates to an improved enzymatic immunoassay and reagents therefor. More particularly, it relates to a stable conjugate of peroxidase with an allergen, a non-immunoglobulin protein or a primary amino group containing drug and the preparation thereof using phenylisothiocyanate as a blocking agent and reduction by titration. The invention is also concerned with an enzyme immunoassay in which serum or tissue is contacted with antibody and the resulting material is then contacted with the stable enzyme-antigen conjugate.

DESCRIPTION OF THE INVENTION

In the following description, the term allergen refers to a partially purified fraction obtained from crude allergenic extracts, which fraction is enriched for the allergenic factor as a result of purification.

The method of the present invention can be performed with any biologic fluid of the patient to be tested. Thus, blood and suitable fluids include nasal, bronchial, middle ear, gastric and lacrimal secretion. The method of the present invention is also applicable to tissue samples.

In the following description, the invention will be described in terms of the detection of IgE but it will be appreciated that this is for convenience only and other immunoglobulins, non-immunoglobulin proteins and primary amino group containing drugs can also be determined.

In the first step of the process, the biologic fluid or tissue is contacted with antibody for the materials sought to be detected, e.g. anti-human IgE. When a biologic fluid is being tested, the anti-IgE should be bound to a substrate. Any substrate can be used such as cellulose or other cellulostic materials such as paper or synthetic supports in the form of tubes, microtiter plates or other physical form of material such as nylon, polystyrene, polypropylene or polycarbonate, and biological material such as red blood cells. Some of the solid phase media with anti-IgE fixed thereon are available in commerce. When a tissue sample is being examined, the tissue itself will be the solid phase. The length of contact should be sufficient to permit the reaction between IgE in the biologic fluid or tissue and the anti-IgE and is generally about 0.1-10 hours or more.

After the contacting, the solid phase is preferably, although not necessarily, washed to remove unbound material with any suitable buffer, such as phosphate buffered saline having a pH of about 7.4.

In the next step of the process, the solid phase is contacted with a peroxidase conjugated suspected allergen for a time sufficient to permit the reaction between the enzyme marked allergen and the IgE bound to the substrate. Generally, incubation is permitted to proceed for about 1–4 hours, preferably about two hours, at room temperature (temperature range 20°–25° C.) and in the presence of an optional incubation buffer such as the aforementioned phosphate buffered saline with or without additives. It will be recognized that variation in the incubation time and conditions are possible and the same is well within the skill of those in this art. Following the incubation, the substrate is again washed with a suitable buffer such as the buffer heretofore mentioned.

The enzymatic activity of the solid phase substrate can now be determined by a variety of procedures known in the art. One procedure which is presently preferred involves the contacting of the substrate with a chromogenic system which will react with the conjugated enzyme to develop color. Any chromogenic reagent which reacts with the conjugate to develop color can be employed in this step. The reagent presently preferred contains hydrogen peroxide and o-phenylene diamine. Other chromogenic systems include p-phenylenediamine, 5-aminosalicylic acid, o-dianisidine, pyrogallol and the like. The reagent is conveniently employed in the form of a solution in any inert carrier such as phosphate buffered saline or other suitable buffer. The substrate is contacted with the chromogenic reagent for a time sufficient to allow color to develop which is usally about 0.1–3 hours, and preferably about 0.5–1.25 hours. The contacting temperature is preferably ambient. Results can be noted by simple observation or by the use of automatic equipment which measures absorbence at the absorption maximum of the reaction product (e.g. 492 nm for o-phenylenediamine) against a blank reagent and provide a net value.

As regards the histochemical localization of a given antigen in tissue is concerned, this method is employed with some modifications. For example, if one were seeking to determine whether certain cells or organelles in cells in a given tissue section contained insulin, the tissue section would be contacted with an antibody to insulin, in excess, so that the specific anti-insulin antibodies bind to tissue insulin through one Fab only, leaving the other free. In the second step of the process, peroxidase labeled insulin is contacted with the tissue section, whereby the enzyme label binds through the free Fab, and an analysis is made for the presence of bound enzyme label. Due to the bivalent nature of the antibody for the antigen, specificity of localization is assured. Impurities in the antibody preparation which nonspecifically bind to tissue components do not interfere, since these do not, and cannot bind the enzyme-labeled insulin.

In order to obtain a high degree of quantification, sensitivity and absence of non-specific reaction in the solid phase immunoenzymatic determination of IgE, it is necessary that the enzyme be peroxidase, and preferably horseradish peroxidase (HRPO). The peroxidase is conjugated to the allergen by first blocking the free amino groups on the peroxidase molecule with a blocking agent, then oxidizing the carbohydrate moiety with periodate to yield the peroxidase aldehyde, and after dialysis, the peroxidase aldehyde is linked to the allergen by formation of a Schiff's base which is thereafter stabilized by reduction with a suitable reagent such as sodium borohydride or sodium cyanoborohydride.

In the reagent preparation just described, it is necessary that the blocking agent be phenylisothiocyanate. The use of conventional blocking agents such as fluorodinitrobenzene result in non-specific reaction, presumably because of the increased negative charge on the enzyme molecule, when the immunoenzymatic test is carried out. The blocking agent is prepared as a solution in absolute alcohol since it is easily soluble in this organic solvent, and when added as an ethanolic solution to the peroxidase solution, the low concentration of ethanol introduced will not be harmful to the enzyme. In order to minimize the removal of excess blocking agent, the agent is added drop by drop while stirring the receiving enzyme solution until a slight cloudiness is observed in the reaction mixture, which indicates an excess of the reagent.

A second important aspect of the preparation of the conjugate regards the borohydride reduction. It is known that samples of sodium borohydride are somewhat unstable being particularly sensitive to exposure to moisture. As a result, a sample of sodium borohydride gradually deteriorates in its reducing power depending on conditions of storage and depending on how many times the container in which it is has been opened and closed between uses. For the reduction of the Schiff's base formed between the allergen and the peroxidase aldehyde, it is necessary that the optimal amount of reducing power derived from the borohydride be used, since a lower amount reduces the efficiency of conjugation and an excess leads to the formation of insoluble aggregates, and thus decreases the final yield of useful conjugate. Adding a predetermined amount of sodium borohydride to the peroxidase aldehyde-allergen will result in conjugates in differing yields from time to time. Therefore, to the peroxidase aldehyde solution, to which has been added at the appropriate amount of allergen, small quantities of the borohydride solution are added, drop by drop, until the color of the mixture develops a slight reddish tinge. This titration procedure compensates for the strength of the reducing agent.

While we have previously shown that this method of preparation could be used to form a stable conjugate between HRPO and the IgG fraction of anti-human IgE, it was particularly surprising that the procedure can also be used to provide a stable peroxidase-allergen conjugate. The immunoglobulins and their antibodies are fairly well defined and are obtainable in purified form. It is known that the antibodies have bonding sites available for conjugation which are physically separated from the site where the anitbody binds to an antigen. Moreover, the antibodies generally have weights of about 160,000 daltons while peroxidase is about 40,000 and the small size of the peroxidase relative to the antibody therefore is not expected to cause a significant distortion in the spatial configuration of the antibody or interfere with its antigen bonding site. In contrast, an allergen is some factor which is present and causes an allergic reaction. Allergens are generally believed to be proteins, though this has not yet been established in all instances. The physical and chemical nature of allergens is not yet defined and the allergens are available only as crude extracts which contain a variety of substances, one or a combination of which may be the factor which causes the allergic reaction. It was not known whether the sites available for conjugation and the sites available for binding to the antibody were sufficiently separated to permit HRPO conjugation without destroying the activity of the allergen. While it has previously been known that the allergen can be labeled with radioactive iodine, the HRPO molecule is about 320 times larger than the iodine. Moreover, since the exact size of different allergens is unknown, it was not known whether the conjugation with the large peroxidase molecule would cause the allergen molecule to deform and deactivate.

Our experience suggests that the allergenic factor(s) present in commercially available crude extracts of grasses, animal danders, tree pollens and weed pollens are at least 12,000 daltons in size. Purified antigen E from ragweed has been known to be about 30,000 daltons. For allergens with average molecular weight in the range of about 30,000 daltons, we find that an average of two to three molecules of HRPO can be conjugated to the allergen without inactivating it, provided that the crude allergen extract available in commerce is partially purified so as to remove the low-molecular weight substances contained therein, and then salt-fractionated to enrich for the allergen. This purification can be easily accomplished by dialysis, followed by precipitation with ammonium sulfate, and a second dialysis. When the conjugate is prepared as described above, the allergen remains biologically recognizable by the IgE in the serum.

Because of the high degree of quantification, sensitivity and the absence of non-specific reaction, it is possible to identify a safe initial hypersensitization dosage amount from the results of the above described test. Heretofore such therapy has been carried out starting with extremely dilute dosage which was increased with the passage of time. As is apparent, relatively weak atopic patients can tolerate a higher dosage and in fact, the higher dosage is necessary in order to realize the desired hypersensitization results. However, since there was no way to determine whether a greater dosage level would be safe for the patient, it was necessary to begin therapy with an extremely dilute amount.

It has been found that serum samples tested by the above described method can be divided into five distinct groups. Those serums whose net absorbence (sample minus control) fall within the range of 0.01-0.05 are considered negative results. For a net absorbence of 0.05-0.15, the results are very weakly positive. An absorbence of 0.15-0.3 is considered weakly positive, from 0.3-0.6 positive and greater than 0.6 strongly positive. Individuals whose sera test in the negative group usually do not require hypersensitization treatment. Those in the very weakly positive group are usually provided with treatment only if their history so indicates and in that case, the initial dosage is the same as that for the weakly positive group. Atopic individuals whose sera test in the weakly positive group can receive hypersensitive treatment at 1:500 w/v safely, those in the positive group can receive 1/5000 w/v safely and those in the strongly positive group can usually receive 1/50,000 w/v safely.

In our work, we have preferred to use rabbit antihuman IgE because it has been found that a significant loss of the test specificity may result from the presence of heterophile antibodies in the test serum which may non-specifically bind the goat or sheep immunoglobulins to the allergen. The use of chick serum has been found quite suitable for the dual purpose of maintaining the optimum protein concentration as the sample is diluted with the incubation buffer and for reducing the non-specific cross-reactivity between the various proteins in the sample and the antiserum. Aprotinin (Trasylol) is preferably added to the incubation buffer to inhibit any protease activity that may exist in the system.

Horse radish peroxidase (crystalline enzyme, Sigma Type VI, RZ3.0 or higher; used in our work samples with RZ of 3.47) was dissolved in 0.1 M sodium carbonate-bicarbonate buffer, pH 9.5 to a final concentration of 5 mg enzyme per ml. To this was added a freshly made solution of phenylisothiocyanate 1% v/v in absolute ethanol, drop by drop (while constantly stirring the enzyme solution gently at room temperature) until a slight cloudiness developed. Usually 0.03 to 0.04 ml of a 1% solution of PITC is needed to achieve this cloudiness per ml of HRP solution 5 mg/ml. It is left standing at room temperature while gently stirring for 2 hrs. If a precipitate, due to an excess of the blocking reagent, appears at this stage, it can be safely removed by centrifugation, and the clear supernatant used for further processing without any significant loss of efficacy of the enzyme. To the enzyme with its free amino groups blocked as mentioned above, was added a 0.06 M sodium periodate solution drop by drop to a final concentration of about 0.03 M thus oxidizing the vicinal dihydroxy groups on the carbohydrate moiety of the enzyme to generate free aldehyde groups. The periodate oxidation, which is time and concentration dependent, is terminated at the end of 20′ by the addition of an excess of ethylene glycol which serves to exhaust the unused periodate. This mixture is then dialysed against 1 mM NaOACHOAC buffer to remove all the micromolecular products of the reaction (nolecules smaller than 12,000 daltons).

Allergen extracts (June and Timothy grasses at 7,000 pnu/ml) were dialysed overnight against 500 volumes of phosphate buffered saline containing 0.1 mM merthiolate with two changes and were further purified with ammonium sulfate precipitation at 50% saturation. 50% ammonium sulfate has been found to yield a purified extract preparation giving the highest absorbence with positive sera and lowest values for the negative controlled seras using the immunoperoxidase assay.

The dialysed peroxidase aldehyde is mixed with the purified allergenic extract in amounts sufficient to bind an average of 2–3 peroxidase molecules to each molecule of allergen with an average molecular weight of about 30,000 daltons. The proportion of enzyme to allergen molecules may be suitably changed depending upon the actual size of the allergen. The resulting Schiff's base is stabilized by reduction with sodium borohydride under optimum conditions. (Typically in a sample starting with 5 mg HRPO and 2.5 mg allergen, one needs about 0.5–0.8 mg $NaBH_4$). To such a reaction mixture is added an equal volume of neutral saturated ammonium sulfate thus precipitating the conjugate, and the precipitated conjugate is separated from unreacted enzyme by centrifugation; the pelleted allergen enzyme conjugate is dissolved in PBS and dialysed against PBS to remove excess salt from the precipitated material. Conjugates prepared by this procedure were found to have an RZ of 1 to 1.2. The conjugates maintain their immunologic reactivity and enzyme activity for several months when stored at or below $-20°$ C.

Commercially available polystyrene Microtiter plates were coated with an IgG fraction purified from rabbit antihuman IgE antiserum by incubating each well with two ug of the IgG in 200 ul of coating buffer (sodium carbonate-bicarbonate) overnight at 4° C. Cord sera was used as a negative control. Additional negative controls were established by using sera from patients who had negative Modified RAST test results for June and Timothy grass antigens.

To assure the specificity of the antibody being detected, an absorption study was designed by incubating the sera of known allergic patients with high titers of IgE antibodies against June and Timothy grasses with appropriate extracts overnight at 4° C. The absorption was performed at two concentrations of the extract: one with equal volumes of the serum and the extract and the other with the serum to extract ratio at 5:1. Following absorption with the appropriate antigen extract, the serum sample was assayed for allergen-specific IgE antibodies.

To demonstrate the independence of the assay from elevated levels of total serum IgE, sera of two patients with positive Modified RAST results for ragweed and negative Modified RAST results for Timothy and June grass were assayed for IgE antibodies against the grass antigens.

For the assay of IgE antibodies against June and Timothy grass antigens with the immunoperoxidase assay using peroxidase labeled allergens, sera from 30 patients presenting symptoms of inhalent allergy were obtained. The diagnosis of allergy in these patients was established using the Modified RAST test (Class 2 and over) and positive skin tests.

The immunoperoxidase assay was carried out as follows. The polystyrene Microtiter plates were washed with phosphate buffered saline containing 0.1 v/v % Tween 20 and all assays were performed in duplicate. 50 ul of a serum sample and 150 ul an incubation buffer (phosphate buffered saline containing 5% v/v chicken serum, 5% v/v Trasylol, 0.1 v/v % Tween 20 and 0.1 mM merthiolate, pH 7.6) were incubated in each well overnight at 4° C. The microplate wells were washed four times with phosphate buffered saline containing 0.1% Tween 20 and 50 ul of peroxidase labeled allergen and 150 ul of the incubation buffer were incubated in each well overnight at 4° C. The wells were washed again four times with phosphate buffered saline-Tween. 200 ul of o-phenylene diamine dihydrochloride, 0.5 mg/ml in McIlvain's buffer (pH 6.0) containing 0.006% of hydrogen peroxide were added to each well and kept at room temperature for one hour. The color reaction was arrested by the addition of 50 ul of 0.5 N $H_2SO_4$ and the absorbence of the color product was measured at 492 nm against the assay reagent blank (prepared by omitting the step of incubation with serum) using a Titertek Multiskan microplate reader.

The impact of dilution upon absorbence has been studied and it has been found that the relationship of the concentration of allergen-specific IgE antibodies correlates directly with the change in the absorbence. Several different sera gave parallel curves.

Cord serum has proven to be an excellent source of negative controlled serum in both the Modified RAST test and in the immunoperoxidase assay of the present invention. In general, absorbence with cord serum ranges from 0.01 to 0.04.

The specificity of the assay for specific IgE antibodies is confirmed with absorption experiments. Pre-incubation of the serum of a June-grass sensitive patient with appropriate (June-grass) extract is able to eliminate the reaction. Pre-incubation of serum with inappropriate (ragweed) extract fails to eliminate the reaction.

FIG. 1 shows the immunoperoxidase assay results for 28 assays with allergic sera, 28 with non-allergic sera and 4 with buffer.

In the foregoing work, polystyrene was used as an immunosorbent because it has been found to give very low non-specific binding of various proteins in the test system. Thus, the absorbence level obtained with the cord serum used as the negative control in this assay are generally in the range of 0.001 to 0.040. The absorbence of negative controlled sera from non-allergic individuals is similarly low. With the element of extraneous proteins causing false positive results kept under control using polystyrene as the immunosorbent, a high degree of test sensitivity and test specificity can be achieved.

It has also been discovered that HRPO can be conjugated to proteins which do not belong to the immunoglobulin class and to a primary amino group containing drug without destroying their biological recognizability by an antibody therefor. Examples of such proteins include albumin, complement components, fibrinogen, transferrin, lysozyme, peptide hormones and examples of such drugs include dopamine and steroid derivatives. It will be appreciated that if the drug contains a latent primary amino group, i.e. a primary amino group which can be produced by suitable treatment of the drug, a stable conjugate can also be formed. As the case with the allergen, conjugation interfering matter should be removed from the protein or drug by appropriate purification procedures.

Various changes and modifications can be made in the process and products of this invention without departing from the spirit and scope thereof. The various embodiments which have been disclosed herein were for the purpose of further illustrating the invention but were not intended to limit it.

What is claimed is:

1. A stable conjugate of peroxidase with a substance selected from the group consisting of allergen, nonimmunoglobulin protein and primary amino group containing drug, said conjugate having an average of 2-3 molecules of peroxidase per molecule of substance with an average molecular weight of about 30,000 daltons, prepared by reacting peroxidase which has previously been treated with phenylisothiocyanate to block its free amino groups and oxidized to form aldehyde groups from its carbohydrate moiety with said substance to form a Schiff's base which is titrated with a reducing agent to form the stable conjugate.

2. The stable conjugate of claim 1 wherein said substance is allergen.

3. The stable peroxidase allergen conjugate of claim 2 having an RZ value of 1.0–1.2.

4. An enzyme immunoassay for detecting an antigen in a biologic fluid or tissue comprising contacting said fluid or tissue with antibody specific for said antigen under binding conditions, at least one of said fluid or tissue and antibody having a solid component, contacting the resulting solid with the conjugate of claim 1 bindable by said antibody under binding conditions, said bindable material is selected from the group consisting of allergen, nonimmunoglobulin protein and primary amino and determining the enzyme activity of the resulting solid phase.

5. The method of claim 4 wherein said antigen is an immunoglobulin and said substance is an allergen.

6. The method of claim 5 wherein said biologic fluid or tissue is serum.

7. The immunoassay of claim 5 wherein the presence of enzyme is determined by measuring absorbence at 492 nm.

8. The method of claim 7 wherein the net increase of absorbence compared to a control is used to establish an initial hyposensitization therapy dosage level.

9. The enzyme immunoassay of claim 5 wherein said biologic fluid or tissue is tissue.

10. A method of preparing a stable conjugate of peroxidase with a substance selected from the group consisting of allergen, non-immunoglobulin protein and primary amino group containing drug comprising obtaining a purified quantity of said substance, blocking the free amino groups on the peroxidase with a blocking agent, oxidizing the carbohydrate moiety of the peroxidase to yield the corresponding aldehyde, dialysing the aldehyde and thereafter linking the aldehyde to the purified substance by formation of a Schiff's base and stabilizing the Schiff's base by reduction, wherein the blocking agent is phenylisothiocyanate and the stabilizing reduction is controlled by titration.

11. The method of claim 10 wherein said substance is allergen and is purified by dialysis and salt fractionation.

* * * * *